United States Patent [19]

Isshiki et al.

[11] Patent Number: 4,517,377

[45] Date of Patent: May 14, 1985

[54] PROCESS FOR PRODUCING VINYL ACETATE

[75] Inventors: Tomiya Isshiki; Takanari Nawata, both of Tokyo; Yasuhiko Kijima; Akira Ito, both of Chiba; Takayuki Watanabe, Tokyo, all of Japan

[73] Assignee: Mitsubishi Gas Chemical Company, Inc., Tokyo, Japan

[21] Appl. No.: 390,074

[22] Filed: Jun. 18, 1982

[30] Foreign Application Priority Data

Jun. 22, 1981 [JP] Japan ................................. 56-96296

[51] Int. Cl.$^3$ ..................... C07C 67/297; C07C 69/15
[52] U.S. Cl. ................................. 560/261; 560/248; 562/607; 562/608
[58] Field of Search ........................ 560/261; 562/607

[56] References Cited

U.S. PATENT DOCUMENTS 2,415,378  2/1947  Vaughn ............................... 560/261
2,425,389  8/1947  Axley et al. ........................ 560/261
3,689,535  9/1972  Kollar ................................. 560/261

*Primary Examiner*—Vivian Garner
*Attorney, Agent, or Firm*—Wenderoth, Lind & Ponack

[57] ABSTRACT

A process for producing vinyl acetate which comprises decomposing ethylidene diacetate in the presence of at least one compound selected from fluorides, bromides, chlorides, iodides, halogens and mixtures thereof is disclosed. According to this invention decomposition rate of ethylidene diacetate is high and selectivity to vinyl acetate is also high.

18 Claims, No Drawings

PROCESS FOR PRODUCING VINYL ACETATE

BACKGROUND OF THE INVENTION

This invention relates to a process for producing vinyl acetate which comprises decomposing ethylidene diacetate, and particularly relates to a process for producing vinyl acetate which comprises carrying out decomposition of ethylidene diacetate in the presence of a catalyst comprising at least one compound selected from the group consisting of fluorides, chlorides, bromides, iodides, halogens and mixtures thereof.

Vinyl acetate has been produced from acetylene in the past. Recently vinyl acetate has also been produced from ethylene.

In addition, a process for producing vinyl acetate which comprises producing ethylidene diacetate (1,1-diacetoxy ethane) from acetaldehyde and acetic anhydride, or dimethyl ether or methyl acetate and synthesis gas and causing decomposition of the ethylidene diacetate to form vinyl acetate (refer to hydrocarbon Process, 44 (11) 287 (1965), British Patent No. 1,538,782 and U.S. Pat. Nos. 2,021,698; 2,425,389 and 2,860,159). However, known processes for decomposing ethylidene diacetate were unsatisfactory.

In the prior art, protonic acids, such as sulfuric acid, organic sulfonic acids, etc. have been known as catalysts for decomposing ethylidene diacetate. Decomposition of ethylidene diacetate by using such catalysts is unsatisfactory in respect of decomposition rate and selectivity to product.

SUMMARY OF THE INVENTION

The present inventors carried out research to find a process for efficiently producing vinyl acetate from ethylidene diacetate. As a result, we found novel catalysts for decomposing ethylidene diacetate to form vinyl acetate. This invention is based on this discovery.

An object of this invention is to provide a process for producing vinyl acetate in a high decomposition rate and in a high selectivity.

DETAILED DESCRIPTION OF THE INVENTION

By the "Periodic Table" given in the specification and the claims is meant Periodic Table in "Shin Jikken Kagaku Kohza" vol. 12, 1976 pages 4–5 published by the Japan Chemical Association.

The mechanism of the decomposition of ethylidene diacetate for forming vinyl acetate is not perfectly clear. However, it is believed that the decomposition reaction is expressed by the following equation:

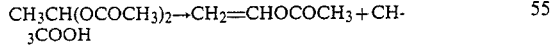

$$CH_3CH(OCOCH_3)_2 \rightarrow CH_2=CHOCOCH_3 + CH_3COOH$$

The above reaction proceeds in a good state when a catalyst comprising a halide is used.

Halides which are usable as the catalyst in the practice of this invention include fluorides, chlorides, bromides, iodides and mixtures thereof. Bromides, iodides and mixtures thereof are preferable; and iodides are most preferable.

The catalysts may be any halogen-containing compounds, such as halogen-containing organic compounds and halogen-containing inorganic compounds, or halogens. Examples of halides include metal halides; halogens; alkyl halides; aryl halides; halides of ammonium, phosphonium, arsonium and stibonium.

Examples of the halides and halogens which are used as the catalyst of this invention are shown in the following. However, compounds which are not listed in the following may also be used as the catalyst.

(I) halides represented by $M_mX_n$ wherein M is a metal belonging to Group IA, IIA, IIIA, IVA, VA, VIA, VIIA, IB, IIB, IIIB, IVB, VB or VIB of the Periodic Table, X is F, Cl, Br or I, m is an integer of 1–4 and n is an integer of 1–7.

(1) Halides of metals belonging to IA include LiF, LiCl, LiBr, LiBr$_2$.2H$_2$O, LiI, LiI.3H$_2$O, NaF, NaCl, NaBr.2H$_2$O, NaI, NaI.2H$_2$O, KF, KF.2H$_2$O, KCl, KBr, KI, KI$_3$, K[AuBr$_4$], K[AuBr$_4$].2H$_2$O, K$_2$[SnBr$_6$], K[AuCl$_4$], K$_2$[PbCl$_6$], K$_2$[ReCl$_6$], K$_2$[SnCl$_6$], K$_2$[TeCl$_6$], K$_2$SiF$_6$, K$_2$SnF$_6$.H$_2$O, K$_2$TaF$_7$, K$_2$TiF$_6$.H$_2$O, K$_2$ZrF$_6$, KAuI$_4$, RbF, RbCl, RbBr, RbI, RbI$_3$, Rb$_2$TiBr$_6$, Rb$_2$PtCl$_6$, Rb$_2$TiCl$_6$, RbBF$_4$, Rb$_2$SiF$_6$, CsF, CsCl, CsBr, CsBr$_3$, CsBr$_2$Cl, CsBrClI, CsIBr$_2$, CsBrCl$_2$, CsICl$_2$, CsI, CsI$_3$, CsICl$_4$, CsAuCl$_4$, Cs$_2$SnCl$_6$, CsBF$_4$, Cs$_2$GeF$_6$ and Cs$_2$SiF$_6$.

(2) Halides of metals belong to IIA include BeF$_2$, BeCl$_2$, BeBr$_2$, BeI$_2$, MgF$_2$, MgCl$_2$.6H$_2$O MgBr$_2$, MgBr$_2$.6H$_2$O, MgI$_2$, MgI$_2$.8H$_2$O, MgSiF$_6$.6H$_2$O, CaF$_2$, CaCl$_2$, CaBr$_2$, CaI$_2$, CaBr$_2$.6H$_2$O, CaCl$_2$.H$_2$O, CaCl$_2$.2H$_2$O, CaCl$_2$.6H$_2$O, CaI$_2$.6H$_2$O, CaSiF$_6$, CaSiF$_6$.2H$_2$O, SrF$_2$, SrCl$_2$, SrBr$_2$, SrI$_2$, SrBr$_2$.6H$_2$O, SrCl$_2$.6H$_2$O, SrCl$_2$, SrF$_2$, SrSiF$_6$.2H$_2$O, SrI$_2$.6H$_2$O, BaF$_2$, BaCl$_2$, BaBr$_2$, BaI$_2$, BaBr$_2$.2H$_2$O, BaCl$_2$.2H$_2$O, BaI$_2$.2H$_2$O and BaSiF$_6$.

(3) Halides of metals belonging to IIIA include ScF$_3$, ScCl$_3$, ScBr$_3$, ScI$_3$, YF$_3$, YCl$_3$, YBr$_3$ and YI$_3$.

(4) Halides of metals belonging to IVA include TiF$_3$, TiF$_4$, TiCl$_2$, TiCl$_3$, TiCl$_4$, TiBr$_2$, TiBr$_3$, TiBr$_4$, TiI$_2$, TiI$_3$, TiI$_4$, TiBr$_3$.6H$_2$O, ZrF$_2$, ZrF$_4$, ZrCl$_2$, ZrCl$_3$, ZrCl$_4$, ZrBr$_2$, ZrBr$_3$, ZrBr$_4$, ZrI$_3$ and ZrI$_4$.

(5) Halides of metals belonging to VA include VF$_2$, VF$_3$, VF$_4$, VF$_5$, VCl$_2$, VCl$_3$, VCl$_4$, VBr$_2$, VBr$_3$, VBr$_4$, VI$_2$, VI$_3$, VBr$_3$.6H$_2$O, VF$_3$.3H$_2$O and VI$_3$.6H$_2$O.

(6) Halides of metals belonging to VIA include CrF$_2$, CrF$_3$, CrF$_4$, CrF$_5$, CrF$_6$, CrCl$_2$, CrCl$_3$, CrCl$_4$, CrBr$_2$, CrBr$_3$, CrI$_2$, CrI$_3$, [Cr(H$_2$O)$_4$]Cl$_2$.2H$_2$O, MoF$_3$, MoF$_5$, MoF$_6$, MoCl$_2$, MoCl$_3$, MoCl$_4$, MoCl$_5$, MoCl$_2$F$_3$, MoBr$_2$, MoBr$_3$, MoBr$_4$, MoI$_2$, MoI$_3$, MoI$_4$, WF$_4$, WF$_6$, WCl$_2$, WCl$_4$, WCl$_5$, WCl$_6$, WClF$_5$, WBr$_2$, WBr$_3$, WBr$_5$ and WBr$_6$.

(7) Halides of metals belonging to VIIA include MnF$_2$, MnF$_3$, MnF$_4$, MnCl$_3$, MnBr$_2$, MnI$_2$, MnBr$_2$.4H$_2$O, MnCl$_2$.4H$_2$O, MnGaF$_5$.7H$_2$O, MnSiF$_6$.6H$_2$O and MnI$_2$.4H$_2$O.

(8) Halides of metals belonging to IB include CuF, CuF$_2$, CuCl, CuCl$_2$, CuBr, CuBr$_2$, CuI, CuCl$_2$.Cu(OH)$_2$, CuCl$_2$.2H$_2$O, CuF$_2$.2H$_2$O, Cu$_2$SiF$_6$, CuSiF$_6$.4H$_2$O, CuSiF$_6$.6H$_2$O, AgF, AgF$_2$, Ag$_2$F, AgCl, AgBr, AgI, AuF$_3$, AuCl, AuCl$_3$, AuBr, AuBr$_3$, AuI and AuI$_3$.

(9) Halides of metals belonging to IIB include ZnF$_2$, ZnCl$_2$, ZnBr$_2$, ZnI$_2$, ZnF$_2$.4H$_2$O and ZnSiF$_6$.6H$_2$O.

(10) Halides of metals belonging to IIIB include BF$_3$, B$_2$F$_4$, BCl$_3$, B$_2$Cl$_4$, BBr$_3$, B$_2$Br$_4$, BI$_3$, BBrI$_2$, BBr$_2$I, BF$_3$.2H$_2$O, BF$_3$.NH$_3$, AlF$_3$, AlCl$_3$, AlBr$_3$, AlI$_3$, AlBr$_3$.6H$_2$O, AlCl$_3$.6H$_2$O, AlCl$_3$.6NH$_3$, AlF$_3$.H$_2$O, Al$_2$(SiF$_6$)$_3$, AlI$_3$.6H$_2$O, AlF$_3$.3NaF, GaF$_3$, GaCl$_3$, GaBr$_3$, GaI$_3$, Ga(GaBr$_4$), GaBr$_3$.NH$_3$, Ga(-

GaCl₄), Ga(GaI₄), InF₃, InCl, InCl₂, InCl₃, InBr, InBr₂, InBr₃, InI, InI₂, InI₃, InF₃.3H₂O, TlF, TlF₃, TlCl, TlCl₃, TlBr, TlBr₃, Tl₃[TlBr₄], TlI, TlI₃, TlCl₃.4H₂O, Tl₂[GaF₅].H₂O and Tl₂SiF₆.2H₂O.

(11) Halides of metals belonging to IVB include SiF₄, Si₂F₆, SiCl₄, Si₂Cl₆, Si₅Cl₁₂, SiBr₄, Si₂Br₆, Si₃Br₈, Si₄Br₁₀, SiI₄, Si₂I₆, GeF₂, GeF₄, GeCl₂, GeCl₄, Ge₂Cl₆, GeBr₂, GeBr₄, GeI₂, GeI₄, SnF₂, SnF₄, SnCl₂, SnCl₄, SnCl₂I₂, SnBr₂, SnBr₄, SnBrCl₃, SnBr₂Cl₂, SnBr₃Cl, SnBr₂I₂, SnI₂, SnI₄, PbF₂, PbFCl, PbCl₂, PbCl₄, PbBr₂, PbI₂, Pb(BF₄)₂, PbI₂.PbO.H₂O, 2PbCl₂.PbO.H₂O, PbCl₂.PbO.H₂O and PbCl₂.2PbO.

(12) Halides of metals belonging to VB include PF₃, PF₅, PCl₃, PCl₅, P₂Cl₄, PClF₂, PCl₂F, PCl₂F₃, PCl₄F, PBr₃, PBr₅, PBrF₂, PBr₂F, PBr₂F₃, PBr₄F, PI₃, AsF₃, AsF₅, AsCl₃, AsBr₃, AsI₂, AsI₃, SbF₃, SbF₅, SbCl₃, SbCl₅, SbBr₃, SbI₃, SbI₅, BiF₃, BiF₅, BiCl₃, BiBr₃ and BiI₃.

(13) Halides of metals belonging to VIB include SeF₄, SeF₆, Se₂Cl₂, SeCl₂, SeCl₄, SeBr₂, SeBr₄, Se₂Br₂, TeF₄, TeF₆, TeCl₂, TeCl₄, TeBr₂, TeBr₄, TeBr₂Cl₂, TeBr₂I₂ and TeI₄.

Metal halides may be in the state of a hydrate, a double salt or a coordination compound. Mixtures of two or more metal halides may be used. The metal halides may be in the form of solid material, powder or finely divided powder. The metal halides may be supported on a carrier. Metal halides supported on a carrier can easily be separated from the reaction system.

(II) Halogens include F₂, Cl₂, Br₂ and I₂.

(III) Organic halides represented by R¹Xp wherein p is an integer of 1–3 and X is as defined above.
  (1) Compounds wherein R¹ is saturated alkyl having 1–10 carbon atoms or cycloalkyl having 3–10 carbon atoms include CH₃F, CH₃Cl, CH₂Cl₂, CHCl₃, CH₃Br, CH₂Br₂, CHBr₃, CH₃I, CH₂I₂, CHI₃, CH₃CH₂Br, CH₃CH₂I, ICH₂CH₂I and C₆H₁₁I.
  (2) Compounds wherein R¹ is aromatic hydrocarbon having 6–10 carbon atoms include C₆H₅Cl, C₆H₅Br, C₆H₅I and C₆H₄I₂.

(IV) Organic halides represented by R²COX wherein R² is saturated alkyl having 1–10 carbon atoms, cycloalkyl having 3–10 carbon atoms or aryl and X is as defined above include CH₃COCl, CH₃COBr, CH₃COI, CH₃CH₂COI, C₆H₁₁COI and C₆H₅COI.

(V) An onium salt of (i) a nitrogen group compound which is shown below and (ii) HX wherein X is as defined above, or a halide which is selected from (III) or (IV).

Examples of nitrogen group compounds are shown in the following:
(1) Compounds of a trivalent nitrogen group element
Compounds represented by the formula

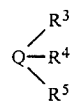

wherein Q is N, P, Sb or As.
  (a) compounds wherein R³, R⁴ and R⁵ may be the same or different, and are independently hydrogen, saturated alkyl having 1–10 carbon atoms, saturated cycloalkyl having 3–10 carbon atoms, or aryl having 6–10 carbon atoms.

Q is N

The compounds include, for example, ammonia, and amines, such as monomethyl amine, dimethyl amine, trimethyl amine, monoethylamine, diethyl amine, triethyl amine, dimethyl ethyl amine, tri-n-propyl amine, tri-isopropyl amine, tri-n-butyl amine, tri-tert.-butyl amine, aniline, dimethyl aniline, diethyl aniline, dimethylbenzyl amine, toluidine, triphenyl amine, cyclohexyl amine and the like.

Q is P

The compounds include, for example, phosphines, such as tri-n-propyl phosphine, tri-iso-propyl phosphine, tri-n-butyl phosphine, tri-tert.-butyl phosphine, tricyclohexyl phosphine, triphenyl phosphine and the like.

Q is Sb

The compounds include, for example, stibines, such as tri-iso-propyl stibine, ethyl-di-iso-propyl stibine, triphenyl stibine, tri(o-tolyl)stibine, phenyl diamyl stibine and the like.

Q is As

The compounds include, for example, arsines, such as trimethyl arsine, triethyl arsine, tri-iso-propyl arsine, tri-n-propyl arsine, tricyclohexyl arsine, phenyl di-iso-propyl arsine, diphenyl arsine and the like.
  (b) wherein R³ is hydrogen, alkyl having 1–10 carbon atoms, cycloalkyl having 3–10 carbon atoms, or aryl and R⁴ and R⁵ are taken together and represent methylene or polymethylene having 2–5 carbon atoms; the compounds include, for example, pyrrolidine, N-methyl pyrrolidine, piperidine or N-phenyl piperidine.
(2) Heterocyclic compounds include, for example, pyridines, such as pyridine; α-picoline, β-picoline, γ-picoline, 2-ethylpyridine, 3-ethylpyridine, 4-ethylpyridine, 2-propylpyridine, 4-propylpyridine, 4-butylpyridine, 4-isobutylpyridine, 4-tert.-butylpyridine, 2,6-lutidine, 2,4-lutidine, 2,5-lutidine, 3,4-lutidine, 3,5-lutidine, 2,4,6-collidine, 2-methyl-4-ethylpyridine, 2-methyl-5-ethylpyridine, 3-methyl-4-ethylpyridine, 3-ethyl-4-methylpyridine, 3,4-diethylpyridine, 3,5-diethylpyridine, 2-methyl-5-butylpyridine, 4-pentylpyridine, 4-(5-nonyl)-pyridine, 2,6-dipropylpyridine, 2-methyl-3-ethyl-6-propylpyridine, 2,6-diethylpyridine, 2,6-dipropylpyridine, 2,6-dibutylpyridine, 2,6-di-tert.butylpyridine; pyrroles; pyrrolines; pyrimidines; pyrazines; pyrazoles; pyrazolines; pyridazines; imidazoles; 1,10-phenanthrolines, such as 1,10-phenanthroline, 4-chloro-1,10-phenanthroline, and 5-(thiapentyl)-1,10-phenanthroline; quinolines, such as quinoline, 2-(dimethylamino)-6-methoxyquinoline, 8-hydroxyquinoline and 2-carboxyquinoline.

Halides represented by (I) M_mX_n and (V) an onium salt of the nitrogen group compound are preferable as the catalyst in respect of its volatility and separation from the product.

Of metal halides represented by M_mX_n, halides of metals selected from Li (IA), Mg, Ca, Sr and Ba (IIA), Cr (VIA), Mn (VIIA), Ag (IB), Zn (IIB), In (IIIB), Sn (IVB) and Sb (VB) are preferable. Halides of metals selected from Li, Mg, Ca, Sr, Ba, Zn, Sn and Sb are more preferable, and Li, Mg, Ca, Sr, Ba and Sb are most preferable. Of nitrogen group compounds constituting onium salt, compounds containing nitrogen or phosphorus are preferable, and nitrogen-containing compounds are most preferable. Of course, a mixture of (I) $M_mX_n$ and (V) the onium salt of a nitrogen group compound can be used as the catalyst.

Amount of the catalyst employed depends on whether the catalyst is soluble, insoluble or partially soluble in the reaction system, or whether the reaction is carried out in a fluidized or fixed bed when using an insoluble catalyst. In general, the amount of the catalyst employed may be in the range of $1 \times 10^{-4}$-90 wt %, preferably $5 \times 10^{-3}$-85 wt %, more preferably $1 \times 10^{-2}$-80 wt % and most preferably 0.1–75 wt % on the basis of weight of the reaction solution.

In practicing this invention, the reaction temperature is not critical. In general, the reaction temperature may be within the range of 20° C.–500° C., preferably 60° C.–350° C., more preferably 80° C.–250° C. and most preferably 80° C.–200° C.

Ethylidene diacetate which is used as a raw material in this invention may be prepared by reacting acetaldehyde with acetic anhydride, or by reduction reaction of acetic anhydride with hydrogen. Alternatively, ethylidene diacetate may be prepared by reacting dimethyl ether or methyl acetate with synthesis gas as disclosed in Japanese Patent Publication (Kokai) Nos. 62045/1980, 110647/1981 and 45884/1980 and British Patent No. 1,538,782. Acetaldehyde, acetic anhydride, dimethyl ether, methyl acetate, methyl iodide, etc. may be incorporated in ethylidene diacetate prepared by such methods. However, the ethylidene diacetate containing the components in such an amount that the components are usually incorporated in ethylidene diacetate, that is the ethylidene diacetate containing small amount of the components can be used as a raw material in this invention.

In general, water may be incorporated in the reaction system. Ethylidene diacetate containing low concentration of water is permitted in this invention. The presence of water of more than 10 mol % on the basis of weight of a reaction solution is not preferable in this process, because such a large amount of water causes decomposition of the starting material and the object product.

In general, water content less than 5 mol % is preferable, and water content less than 3 mol % is more preferable. Water is not formed in the reaction. So, substantially anhydrous conditions can be maintained by keeping the starting material and other components added to the reaction system dry.

The present process may be carried out in gaseous or liquid phase. The present process may be carried out by batch, semi-continuous or continuous method. When using catalysts insoluble in the reaction system, either fluidized bed or fixed bed may be used.

Since ethylidene diacetate (starting material) and vinyl acetate (object product) serve as a solvent for the reaction of the present invention, another solvent is not necessary. However, other organic solvents compatible with ethylidene diacetate and products under the reaction conditions may be used. Compounds which participate as solvent in the reaction as a starting material, an object product or a by-product are preferable. For example, ethylidene diacetate and acetic anhydride are preferable.

Solvents which are usable in this invention include, for example, organic acid esters, such as ethylene glycol diacetate, propylene glycol diacetate, methyl acetate, dimethyl adipate, methyl benzoate, ethyl benzoate, dimethyl phthalate, diethyl phthalate, dioctyl phthalate, phenyl acetate and tolyl acetate; hydrocarbons, such as dodecane, hexadecane, benzene, naphthalene, and biphenyl; inorganic acid esters, such as triphenyl phosphate, tricresyl phosphate, dibutylphenyl phosphate, tetramethyl ortho silicate, and tetrabutyl silicate; aromatic ethers, such as diphenyl ether; and ketones, such as acetone, methyl ethyl ketone, dibutyl ketone, methyl isobutyl ketone, acetophenone and benzophenone.

It is desirable in the present invention that the concentration of vinyl acetate, which tends to cause polymerization, be maintained at a low level by separating the vinyl acetate from the reaction system. For example, it is suitable to maintain the concentration of vinyl acetate in the reaction system at less than 25 wt % by continuously withdrawing (for example distilling) the resulting vinyl acetate from the reaction system and it is preferable to maintain the concentration at less than 15 wt %.

Retention of large amount of the acetic acid, which is formed as a by-product in the reaction system, should be avoided. The reason is that acetic acid tends to prevent formation of the object product. So, in general, the concentration of acetic acid in the reaction system may be no more than 50 wt %, preferably less than 40 wt %, more preferably less than 30 wt % and most preferably less than 20 wt %.

It is preferable that the decomposition of ethylidene diacetate is carried out while continuously withdrawing from the reaction system vinyl acetate and acetic acid formed. Vinyl acetate and acetic acid may be withdrawn from the reaction system by distillation. Withdrawal of vinyl acetate and acetic acid can be made by withdrawing some of the reaction solution containing vinyl acetate and acetic acid from the reaction system.

The following examples are given as illustrative embodiments of the invention and should not be construed as limiting its scope. All parts and percents are by weight, unless otherwise specified.

EXAMPLE 1

Into a reactor were charged 135 grams of ethylidene diacetate and 4.5 g of lithium iodide. After the reactor had been purged with nitrogen, the reactor was sealed. The reaction was carried out at 175° C. for 90 minutes with stirring. After cooling, analysis showed that 5.56 g of vinyl acetate and 3.96 g of acetic acid were formed.

EXAMPLES 2–27

The procedures of Example 1 were repeated by using the reaction conditions and the components as given in Table 1.

TABLE 1

| Ex. No. | Ethylidene diacetate (g) | Catalyst | (g) | Reaction temperature (°C.) | Reaction time (min.) | Amount of vinyl acetate formed (g) |
|---|---|---|---|---|---|---|
| 2 | 135 | LiBr.H$_2$O | 4.5 | 175 | 90 | 4.24 |
| 3 | " | LiCl | 4.5 | " | " | 0.057 |
| 4 | " | KI | 4.5 | " | " | 0.063 |
| 5 | " | CsI | 4.5 | " | " | 0.086 |
| 6 | " | MgI$_2$ | 4.5 | " | " | 0.664 |
| 7 | " | CaI$_2$.4H$_2$O | 4.5 | " | " | 2.31 |
| 8 | " | SrI$_2$ | 4.5 | " | " | 3.60 |
| 9 | " | BaI$_2$.2H$_2$O | 4.5 | " | " | 5.84 |
| 10 | 135 | BaI$_2$.2H$_2$O | 24.6 | 175 | 15 | 4.99 |
| 11 | " | BaCl$_2$.2H$_2$O | 4.5 | " | 90 | 4.24 |

TABLE 1-continued

| Ex. No. | Ethylidene diacetate (g) | Catalyst | (g) | Reaction temperature (°C.) | Reaction time (min.) | Amount of vinyl acetate formed (g) |
|---|---|---|---|---|---|---|
| 12 | " | TiI$_4$ | 4.5 | " | " | 0.174 |
| 13 | " | CrI$_3$.9H$_2$O | 4.5 | " | " | 0.260 |
| 14 | " | MnI$_2$ | 4.5 | " | " | 0.573 |
| 15 | " | CuI | 4.5 | " | " | 0.125 |
| 16 | " | AgI | 4.5 | " | " | 0.508 |
| 17 | " | ZnI$_2$ | 4.5 | " | " | 0.876 |
| 18 | " | AlI$_3$ | 4.5 | 145 | " | 1.65 |
| 19 | " | InI | 4.5 | 175 | " | 0.582 |
| 20 | " | SnI$_4$ | 4.5 | " | " | 1.44 |
| 21 | " | PbI$_2$ | 4.5 | " | " | 0.113 |
| 22 | " | SbI$_3$ | 4.5 | " | " | 2.38 |
| 23 | " | BiI$_3$ | 4.5 | " | " | 0.205 |
| 24 | " | NH$_4$I | 4.5 | " | " | 2.74 |
| 25 | " | (CH$_3$)$_4$NI | 4.5 | " | " | 0.038 |
| 26 | 135 | CH$_3$I | 15 | 175 | 90 | 1.30 |
| 27 | " | I$_2$ | 4.5 | " | " | 0.263 |

EXAMPLE 28

Into a reactor were charged 75 g of ethylidene diacetate, 75 g of acetic anhydride and 4.5 g of barium iodide dihydrate. The reaction was carried out at 175° C. for 90 minutes. 4.76 g of vinyl acetate was formed.

EXAMPLE 29

Into a reactor equipped with agitating blade and filter were charged 15 g of barium iodide dihydrate and 135 g of ethylidene diacetate. After the reactor was purged with nitrogen, the reaction had been carried out at 175° C. for 15 minutes. The reaction was further carried out at 175° C. for 3 hours while continuously feeding ethylidene diacetate into the reactor at a rate of 500 g/hour and continuously withdrawing the reaction solution from the reactor through the filter. 32.2 g of vinyl acetate was obtained by distilling the reaction solution withdrawn from the reactor.

EXAMPLE 30

Into an autoclave were charged 105 g of ethylidene diacetate and 40 g of barium iodide dihydrate. Th autoclave was closed. The contents in the autoclave were heated and stirred at 160° C. for 14 minutes. A mixture of ethylidene diacetate and acetic anhydride (37:63 by weight) was fed at rate of 42 g/hour into the autoclave with stirring while maintaining the contents at 160° C. and at the same time vapor was withdrawn from the autoclave at rate of 42 g/hour. The operation was continued for 6 hours. 26.5 g of vinyl acetate was obtained by distilling the distilate.

EXAMPLE 31

Into an autoclave were charged 105 g of ethylidene diacetate, 195 g of acetic anhydride and 40 g of lithium iodide. The autoclave was closed, and heated. The contents in the autoclave were stirred at 160° C. for 19 minutes. A mixture of ethylidene diacetate and acetic anhydride (37:63 by weight) was fed at rate of 57 g/hour into the autoclave with stirring while maintaining the contents at 160° C. and simultaneously vapor was withdrawn from the autoclave at rate of 57 g/hour. The operation was continued for 7.5 hours. 53.2 g of vinyl acetate was obtained by distilling the distillate.

What is claimed is:

1. A process for producing vinyl acetate which comprises decomposing ethylidene diacetate in a liquid phase at a temperature within the range of 80° to 250° C. in the presence of at least one halide compound selected from the group consisting of:
   (a) metal halides selected from the group consisting of bromides and iodides of metals, and mixtures thereof, said metal being selected from the group consisting of Li, Mg, Ca, Sr, Ba, Zn, Sn and Sb;
   (b) organic halides represented by R$^1$Xp wherein R$^1$ is selected from alkyl having 1-10 carbon atoms, cycloalkyl having 3-10 carbon atoms or aromatic hydrocarbon having 6-10 carbon atoms, X is selected from I, Br, F or Cl and p is an integer of 1-3;
   (c) organic halides represented by R$^2$COX wherein R$^2$ is selected from alkyl having 1-10 carbon atoms, cycloalkyl having 3-10 carbon atoms or aryl, and X is as defined above; and
   (d) onium salts of (i) a nitrogen group compound and (ii) HX wherein X is as defined above, or a halide represented by R$^1$Xp or R$^2$COX wherein X, R$^1$, R$^2$ and p are as defined above.

2. The process as defined in claim 1 wherein said metal halide is a metal iodide.

3. The process as defined in claim 2 wherein the metal constituting said metal halide is selected from the group consisting of Li, Mg, Ca, Sr, Ba and Sb.

4. The process as defined in claim 1 wherein said metal halide is selected from the group consisting of LiI, LiBr, MgI$_2$, MgBr$_2$, CaI$_2$, CaBr$_2$, SrI$_2$, SrBr$_2$, BaI$_2$ and BaBr$_2$.

5. The process as defined in claim 1 wherein said halide is an onium salt of (i) a nitrogen group compound and (ii) HX wherein X is as defined above, or a halide represented by R$^1$X$_p$ or R$^2$COX wherein X, R$^1$, R$^2$ and p are as defined above.

6. The process as defined in claim 5 wherein said nitrogen group compound is selected from compounds of a trivalent nitrogen group element.

7. The process as defined in claim 6 wherein said compound is a compound of a trivalent nitrogen group element represented by the formula:

$$Q \diagup\!\!\!\begin{array}{l}R^3 \\ -R^4 \\ R^5\end{array}$$

wherein Q is selected from the group consisting of N, P, Sb and As, and R$^3$, R$^4$ and R$^5$ are the same or different and are independently hydrogen, alkyl having 1-10 carbon atoms, cycloalkyl having 3-10 carbon atoms or aryl having 6-10 carbon atoms, or R$^3$ is as defined above and R$^4$ and R$^5$ are taken together to form methylene or polymethylene having 2-5 carbon atoms.

8. The process as defined in claim 6 wherein said compound of a trivalent nitrogen group element is a heterocyclic compound.

9. The process as defined in claim 5 wherein said onium salt is NH$_4$I.

10. The process as defined in claim 1 wherein the amount of said halide compound employed is in the range of $1 \times 10^{-4}$-90% by weight on the basis of weight of the reaction solution.

11. The process as defined in claim 10 wherein the amount of said compound employed is in the range of $1 \times 10^{-2}$-80% by weight on the basis of weight of the reaction solution.

12. The process as defined in claim 1 wherein the reaction is carried out while withdrawing vinyl acetate and/or acetic acid from the reaction system.

13. The process as defined in claim 12 wherein the withdrawal of vinyl acetate and/or acetic acid is made by distillation.

14. The process as defined in claim 1 wherein the reaction is carried out while maintaining the concentration of vinyl acetate at less than 25% by weight by withdrawing vinyl acetate from the reaction system.

15. The process as defined in claim 14 wherein the concentration of vinyl acetate in the reaction system is maintained at less than 15% by weight.

16. The process as defined in claim 1 wherein the reaction is carried out while maintaining the concentration of acetic acid at less than 50% by weight by withdrawing acetic acid from the reaction system.

17. The process as defined in claim 16 wherein the concentration of acetic acid in the reaction system is maintained at less than 20% by weight.

18. The process as defined in claim 1 wherein said reaction temperature is between 80° and 200° C.

* * * * *